United States Patent [19]

Stefanelli et al.

[11] Patent Number: 5,854,036
[45] Date of Patent: Dec. 29, 1998

[54] SESQUITETERPENIC DERVATIVES

[75] Inventors: Stefania Stefanelli, Legnano; Federica Sponga, Saronno; Khalid Islam, Como, all of Italy; Maurizio Denaro, Del Mar, Calif.; Pietro Ferrari, Garbagnate, Italy

[73] Assignee: Gruppo Lepetit S.p.A., Milan, Italy

[21] Appl. No.: 716,259

[22] PCT Filed: Mar. 21, 1995

[86] PCT No.: PCT/EP95/01045
§ 371 Date: Sep. 10, 1996
§ 102(e) Date: Sep. 10, 1996

[87] PCT Pub. No.: WO95/26344
PCT Pub. Date: Oct. 5, 1995

[30] Foreign Application Priority Data

Mar. 25, 1994 [EP] European Pat. Off. ............. 94104783

[51] Int. Cl.$^6$ .......................... C12D 17/04; A16K 31/34; C07D 307/94
[52] U.S. Cl. .......................... 435/126; 514/462; 549/345; 435/171
[58] Field of Search .......................... 549/345; 514/462; 435/126, 171

[56] References Cited

U.S. PATENT DOCUMENTS 4,229,466 10/1980 Miyazaki et al. .
4,981,980 1/1991 Giacobbe et al. .

OTHER PUBLICATIONS

Ayer, etal., Candian J. of Chemistry, 71(4):487–493 (1993), "Secondary metabolites of cylindrospora".

Kaneto, et al. The J. of Antibiotics, 47(6):727–730 (1994), "Mer–NF5003B, E and F Novel Sesquiterpeniods as Avian Myeloblastosis Virus Protease Inhibitors Produced".

Chemical Abstract # 94–252805/31 TANB 92.03.04, Tokyo Tanabe Co. JP. 06184133–A, Novel cholesterol esterase Inhibitors–useful for treating hyprocholesterolaemia (1992).

Primary Examiner—Johann Richter
Assistant Examiner—Taofiq A. Solola
Attorney, Agent, or Firm—Ruth E. Homan

[57] ABSTRACT

The present invention concerns novel compounds obtained by fermenting a microorganism of the genus Memnonoiella or Stachybotrys, which compounds are inhibitors of the enzyme inositol monophosphatase (EC 3.1.3.25). The present invention also relates to the use of these novel compounds in treating manic depression and pharmaceutical formulations comprising said compounds as active ingredient; a further object is the use of these compounds in an analytical method for detecting inositol monophosphatase.

12 Claims, No Drawings

SESQUITETERPENIC DERVATIVES

The present invention concerns novel compounds obtained by fermenting a microorganism of the genus Memnoniella or Stachybotrys, which compounds are inhibitors of the enzyme inositol monophosphatase (EC 3.1.3.25), hereinafter referred to with the acronym "IMPase".

The present invention also relates to the use of these novel compounds in the treatment of mania and depression symphtoms and pharmaceutical formulations comprising said compounds as active ingredient; the compounds of the invention may also be used in analythical methods for detecting IMPase.

The invention is also concerned with the fermentation and purification process by which the novel compounds are obtained.

Lithium, preferably employed in the form of lithium carbonate, is highly specific in alleviating manic symptoms, normalizing the mood of manic patients rather than compensating the excesses of the manic state through sedation or "tranquillization". Furthermore, it seems to be the only drug in psychiatry for which clear prophylaxis against disease recurrences and deterioration has been demonstrated. Lithium shows its clearest effects in bipolar disorders, which include both mania and depression, or only mania; these disorders are subdivided into Bipolar I and II disorders. In the former cases, there is presence of a full-blown manic episode, while in the latter case there is mild hypomania only.

Despite its therapeutic properties, a number of issues detract from the therapeutic utility of lithium. Antipsychotic drugs are the first pharmacologic mode of treatment of acute bipolar disorder, unless the patient is manageable enough to wait the 7–10 days it takes for lithium to exert its antimanic effect. A costly prelithium workup is required because of the adverse effects common to lithium therapy. As a matter of fact, lithium can cause a transient leukocytosis, can cause patients with a borderline thyroid reserve to become clinically hypothyroid, and can decompensate cardiac status due to shifts in fluids and electrolytes.

It has been observed that the polyuria-polydipsia syndrome occurs in up to 60% of treated patients. Structural lesions in kidney, such as interstitial fibrosis, tubular atrophy and glomerular sclerosis, are reported after chronic lithium treatment, especially in patients who have experienced lithium toxicity. Other adverse effects of lithium include tremor, weight gain, diarrhea and skin rash. These side effects are serious practical deterrents to the use of lithium in clinical practice.

Side effects, especially the more serious ones, can be reduced by monitoring plasma lithium concentrations in bipolar patients. The need to monitor plasma drug concentrations, and to maintain these within a narrow therapeutic range, destract from its clinical utility.

An ideal lithium mimetic agent would have a rapid onset of action in both bipolar and non-bipolar depression, require only once-a-day dosing, and have a safety profile requiring no extensive pretreatment medical evaluation, no plasma drug monitoring, nor be associated with as severe a spectrum of side effects as lithium, per se.

It was demonstrated that inositol monophosphatase is a key enzyme in the phosphoinositide cycle and is responsible for the provision of inositol by dephosphorylation of inositol-1-phosphate, inositol-3-phosphate, and inositol-4-phosphate; as lithium inhibits the activity of said enzyme, it has been suggested that this inhibition is likely to be the molecular mechanism by which lithium exerts its anti-manic and anti-depressive activity.

In this view, development of potent and specific inhibitors of IMPase, could lead to completely novel drugs effective for the treatment of mania and depression.

A compound of formula I,

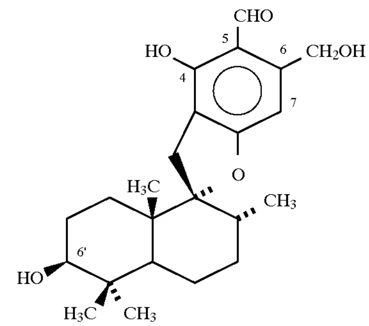

I which shows the above IMPase-inhibiting activity, was obtained by fermenting a fungus of the specie Memnoniella or Stachybotrys as described in U.S. Pat No. 4,981,980. Such compound is also described by Y. K. T. Lam et al. in Jour. of Antib., vol. 45, 9, 1992, pp. 1397–1403, where it is named L-671,776. The above structure seems however to be incorrect as the evaluation of the physico-chemical data suggests that the formyl group at the 5-position is in fact at the 7-position.

H. Kaise et al. in J. C. S. Chem. Comm. (1979) p.726–7 describe the compound K-76, an inhibitor of the complement system which precipitates in rheumatoid arthritis, glomerulonephritis and other immune complex diseases. K-76 was obtained from Stachybotrys complementi nom. nud. sp. K-76 and has the structure II:

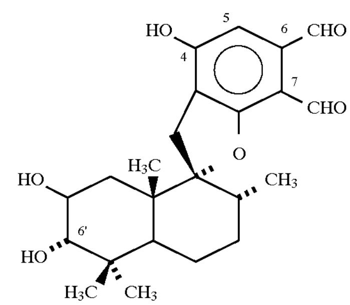

II

Furthermore, by growing the fungus *Stachybotrys cylindrospora* C.N. Jensen N0F1828 in a malt extract/yeast extract liquid culture, a compound of formula III was obtained

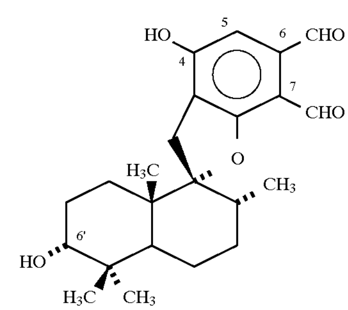

III as disclosed by W. A. Ayer et al. in Can. J. Chem., 71, 1993, 487–493, named Stachybotrydial, for which no pharmaceutical indication has been given.

It has now been found that fermentation of a fungus of the genus Memnoniella or Stachybotrys under suitable aerobic conditions results in a complex of at least three fermentation products, in which the known compound of formula I (L-671,776) is obtained in admixture with two novel compounds, i.e. the 6'β stereoisomer of compound III (Stachybotrydial) and a deformyl-carboxy derivative of the above 6'β-Stachybotrydial, hereinafter named MDL63394.

For the sake of brevity, in the following of this specification, the complex of the three compounds obtained according to the above fermentation will be designated as "IMPase-inhibiting complex", while with the term "IMPase-inhibiting compounds" are intended both 6'β-Stachybotrydial and MDL63394.

Physico-chemical characteristics of 6'β-Stachybotrydial

A) Ultraviolet absorption spectrum:

| Solvent | Lambda max (nm) |
|---------|-----------------|
| MeOH | 222, 284 |
| 0.1 M KOH | 231, 291, 334 |

B) Positive ion FAB spectrum on a Finnigan TSQ 700 triple stage quadrupole mass spectrometer; saddle field atom gun with Xe gas at 8 kV voltage and 0.23 mA current; glycerol/water matrix:

Major FAB/MS peak determined at 387 (MH+)

C) $R_f$ value of 0.48 in the following TLC system:
hexane:acetone, 6:4 (v/v) on silica gel D) NMR spectra recorded in $CDCl_3$ with a Bruker AM 500 instrument, using TMS as internal standard (δ, ppm=0), (s=singlet; d=doublet; br s=broad singlet; m=multiplet):

1H-NMR recorded at 500 MHz, (δ,ppm): 10.65 s, 10.40 s, 6.94 s, 3.41 br s, 3.19 d, 2.84 d, 2.00–1.72 m, 1.70–1.40 m, 1.02 2m, 0.89 s, 0.77 s;

$^{13}C$-NMR recorded at 125.76 MHz, (δ,ppm): 193.5, 188.6, 167.6, 157.5, 138.1, 119.5, 111.5, 109.1, 100.7, 75.7, 42.3, 40.1, 37.6, 37.1, 31.2, 30.7, 28.3, 24.7, 24.2, 22.3, 21.0, 16.1, 15.5.

Physico-chemical characteristics of MDL63394

A) Ultraviolet absorption spectrum:

| Solvent | Lambda max (nm) |
|---------|-----------------|
| MeOH | <200, 275 |
| 0.1 M KOH | <200, 282, 337 |

B) Positive ion FAB spectrum on a Finnigan TSQ 700 triple stage quadrupole mass spectrometer; saddle field atom gun with Xe gas at 8 kV voltage and 0.23 mA current; glycerol/water matrix:

Major FAB/MS peak determined at 403 (MH+)

C) $R_f$ value of 0.23 in the following TLC system: hexane:acetone, 6:4 (v/v) on silica gel On the basis of the above reported physico-chemical data and by comparison with the structure of the known compounds of the fermentation complex, the following formula IV can tentatively be assigned to the novel compounds 6'β-Stachybotrydial and MDL63394

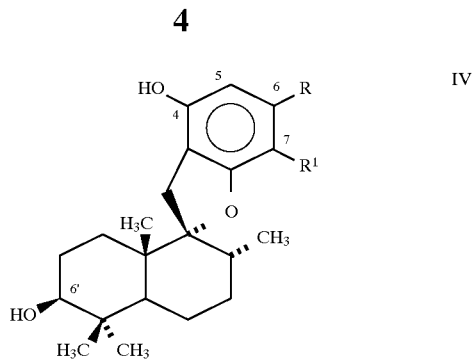

wherein when both R and $R^1$ represent a —CHO moiety, then 6'β-Stachybotrydial is determined, while when one of R or $R^1$ represents a —CHO moiety and the other represents a —COOH moiety, compound MDL63394 is determined.

The process for obtaining the compounds of the invention comprises:
a) Cultivating under aerobic conditions in an aqueous nutrient medium containing assimilable sources of carbon, nitrogen, and inorganic salts a fungus of the genus Memnoniella or Stachybotrys capable of producing the IMPase-inhibiting complex containing the IMPase-inhibiting compounds of the invention;
b) recovering the compounds of the IHPase-inhibiting complex from the fermentation broth and/or from the mycelium;
c) purifying and isolating the compounds of the invention according to known per se techniques.

Preferably, the production of the IMPase-inhibiting compounds of the invention is achieved by cultivating a Memnoniella strain capable of producing them; conveniently, a fungus of the *Memnoniella echinata* species is employed, particularly preferred being *Memnoniella echinata* ATCC 20928.

The fungus *Memnoniella echinata* ATCC 20928 has been deposited without restriction in, and made a part of, the American Type Culture Collection, Rockville, Md., from which it is available under Accession Number ATCC No. 20928.

For the production of the IMPase-inhibiting compounds, the process of the present invention is not limited to the use of *Memnoniella echinata* ATCC 20928. For the fermentation process of the invention, any Memnoniella or *Stachybotrys sp.* or natural or artificial mutants or variants thereof may be used, in so far as they can produce the inositol monophosphatase inhibitors of the invention. The artificial production of mutants may be achieved by conventional operations such as X-ray or ultraviolet irradiation, high frequency waves or radioactive rays, or by the use of chemical mutagens such as nitrogen mustards, nitrous acid, nitrosoguanidine, N-methyl-N'-nitro-N-nitrosoguanidine, and the like.

The medium used for cultivating the "IMPase-inhibiting complex" producing strain may be any fluid or solid medium containing the nutrients which the particular microorganisms are able to utilize, although a fluid medium is preferable for commercial scale operations.

As known in the art, the composition of the nutrient medium may be varied over a wide range. As known in the art, carbon and nitrogen sources are present in the fermentation medium. Typical sources of carbon include: glucose, lactose, maltose, galactose, sucrose, dextrin, fats and oils (e.g. soyben oil, lard oil, chicken oil), starches, glycerol, mannitol, sorbitol and the like. Typical nitrogen sources include: ammonia, ammonium sulfate, amino acids such as glycine, arginine, threonine, methionine, tryptone, peptone, complex sources such as yeast autolysates, malts, soy, cotton seed, tomato paste, corn steep liquor, yeast extract, meat extract and fermentation by-products such as whole yeast and distillers solubles. Other essential nutrients are provided via the mineral salts such as the chlorides, nitrates, sulfates, carbonates and phosphates of sodium, potassium, ammonium, magnesium and calcium. The nutrient medium may also contain sources of inorganic trace elements such as magnesium, iron, copper, manganese, zinc, cobalt, cadmium, molybdenum and the like. It is, of course, possible to add inorganic or organic acids, alkalies, buffers, etc. for the purpose of adjusting the pH of the medium, or to add suitable amounts of oils, surfactants, etc. for defoaming purposes.

Ordinarily, the IMPase-inhibiting complex producing strain is pre-cultured in a shake flask, then the culture is used to inoculate jar fermentors for production of substantial quantities of the IMPase-inhibiting compounds. The medium used for the pre-culture can be the same as that employed for larger fermentations, but other media can also be employed.

The IMPase-inhibiting complex producing strain is grown at temperatures of from 20° C. to 40° C., preferably 24° C. to 35° C., particularly preferred is a temperature of about 25° C.

The fermentation may be carried out by any procedure such as stationary, shake or aerobic stirred culture; preferably shaking or surface culture are employed, particulary preferred being the fermentation on a rotary shaker.

Agitation and aeration of the culture mixture may be accomplished in a variety of ways. Agitation may be provided by a propeller or similar mechanical agitation equipment, by revolving or by shaking the fermentor, by various pumping equipment or by passage of sterile air through the medium. Aeration may be effected by passing sterile air through the fermentation mixture.

During fermentation, the IMPase-inhibiting complex production can be monitored by testing broth or mycelial extract samples for IMPase-inhibiting activity, for instance, by bioassays or TLC or HPLC procedures.

In general, fermentation is completed in about 3 to 5 days.

The recovery of the IMPase-inhibiting complex from the mycelium or the fermentation broths of the producing microorganisms is conducted according to known per se techniques such as extraction with solvents, precipitation by adding non-solvents or by changing the pH of the solution, partition chromatography, reverse-phase partition chromatography, ion-exchange chromatography, molecular exclusion chromatography and the like.

A preferred procedure for recovering the IMPase-inhibiting compounds of the invention involves extracting the filtered or centrifuged mycelium with a water-miscible organic solvent, concentrating the extracts and recovering the crude IMPase-inhibiting compounds by precipitation, optionally with the addition of a precipitating agent, by extraction of the aqueous residue with a water immiscible organic solvent or by adsorption chromatography followed by elution of the desired product from the adsorption matrix.

The term "water-miscible solvent" as used in this application, is intended to have the meaning currently given in the art to this term and refers to solvents that, at the conditions of use, are miscible with water in a reasonably wide concentration range.

Examples of water-miscible organic solvents that can be used in the extraction of the antibiotic substances of the invention from the mycelial mass are: lower alkanols, e.g. ($C_1$–$C_3$)alkanols such as methanol, ethanol and propanol; phenyl($C_1$–$C_3$)alkanols such as benzyl alcohol; lower ketones, e.g. ($C_3$–$C_4$)ketones such as acetone and methyl-ethyl-ketone; cyclic ethers such as dioxane and tetrahydrofuran; glycols and their products of partial etherification, such as ethylene glycol, propylene glycol and ethylene glycol monomethyl ether; lower amides such as dimethylformamide and diethylformamide.

The term "water-immiscible solvent" as used in this application, is intended to have the meaning currently given in the art to this term and refers to solvents that at the conditions of use are slightly miscible or practically immiscible with water in a reasonably wide concentration range, suitable for the intended use.

Examples of water-immiscible organic solvents that can be used in the extraction of the antibiotic substances of the invention from an aqueous phase are: the usual hydrocarbon solvents which may be linear, branched or cyclic such as hexane or cyclohexane; halogenated hydrocarbons such as chloroform, carbon tetrachloride, dichloroethane, fluorobromoethane, dibromoethane, trichloropropane, chlorotrifluorooctane and the like; aromatic hydrocarbons such as benzene, toluene, xylene and the like; esters of at least four carbon atoms, such as ethyl acetate, propyl acetate, ethyl butyrate, and the like; alkanols of at least four carbon atoms which may be linear, branched or cyclic such as butanol, 1-pentanol, 2-pentanol, 3-pentanol, 1-hexanol, 2-hexanol, 3-hexanol, 3,3-dimethyl-1-butanol, 4-methyl-1-pentanol; 3-methyl-1-pentanol, 2,2-dimethyl-3-pentanol, 2,4-dimethyl-3-pentanol, 4,4-dimethyl-2-pentanol, 5-methyl-2-hexanol, 1-heptanol, 2-heptanol, 5-methyl-1-hexanol, 2-ethyl-1-hexanol, 2-methyl-3-hexanol, 1-octanol, 2-octanol, cyclopentanol, 2-cyclopentylethanol, 3-cyclopentyl-1-propanol, cyclohexanol, cycloheptanol, cyclooctanol, 2,3-dimethylcyclohexanol, 4-ethylcyclohexanol, cyclooctylmethanol, 6-methyl-5-hepten-2-ol, 1-nonanol, 2-nonanol, 1-decanol, 2-decanol and 3-decanol; straight or branched alkyl ethers and mixture thereof such as petroleum ether, ethyl ether, propyl ether, butyl ether, etc; and mixtures or functional derivatives thereof.

Examples of precipitating agents are petroleum ether, lower alkyl ethers, such as ethyl ether, propyl ether and butyl ether, and lower alkyl ketones such as acetone. Preferably, ethyl ether is employed.

As known in the art, product extraction may be improved by salting or by adding a proper organic salt forming a ion pair with the antibiotic which is soluble in the extraction solvent.

As known in the art, phase separation may be improved by salting.

Examples of stationary phases which are usefully employed in the above chromatographic adsorption step, for recovering the crude IMPase-inhibiting complex after concentration of the mycelium extracts, are silica gel (e.g. ICN Biomedicals silica 32–62, 60Å), silanized silica gel (e.g. Hibar Lichrosorb RP 18; Beckman Ultrasphere ODS), allumina, diatomaceous earth, carbon, polystyrene resins (e.g. Amberlite XAD2 or XAD4, Rohm and Haas; Dowex M112 or S112, Dow Chemical Co.; Diaion HP 20, Mitsubishi), acrylic resins (e.g. XAD7 or XAD8, Rohm and Haas), polyamide resins such as polycapro-lactames, nylons and cross-linked polyvinylpyrrolidones (e.g. Polyamide-CC 6, Polyamide-SC 6, Polyamide-CC 6.6, Polyamide-CC 6AC and Polyamide-SC 6AC, Macherey-Nagel & Co., West Germany; PA 400, M. Woelm AG, West Germany; and the polyvinylpyrrolidone resin PVP-CL, Aldrich Chemie GmbH & Co., KG, West Germany) and controlled pore cross-linked dextrans (e.g. Sephadex LH-20, Pharmacia Fine Chemicals, Ab). Preferably, polystyrene resin are employed, particularly preferred being the S112 resin.

The preferred solvent for eluting the IMPase-inhibiting complex from the adsorption matrix depends on the specific stationary phase.

For instance, when silica gel or alumina is employed, preferred solvents are halogenated hydrocarbons, lower alkanols, ethers, higher ketones and mixtures thereof; lower ketone such as acetone or a lower alcohol such as methanol may be used with carbon as stationary phase; water-miscible solvents or mixture thereof, such as ethanol, are preferred eluents for polystyrene or acrylic resins, while aqueous mixture of water-miscible solvents are preferred for polyamide resins.

Purification of the crude IMPase-inhibiting compounds is obtained according to known per se techniques, for instance by suspending the crude product in a suitable organic solvent, such as acetone, and removing the precipitate. The single components of the complex are then separated by means of known chromatographic techniques; for instance, XPLC separation systems may be employed, using silica gel as stationary phase and hexane/acetone as mobile phase.

As previously stated, it has been found that both 6'β-Stachybotrydial and MDL63394 show inhibitory activity against the enzyme inositol monophosphastase (EC 3.1.3.25).

For determining said activity, IMPase with a purity higher than 90% as judged by SDS-PAGE (sodium dodecyl sulphate polyacrylamide gel electrophoresis) is purified as described in P. D. Pelton and A. J.

Ganzhorn, Journal Biolog. Chem., 267, 1992, pp. 5916–5920. The enzyme can be purified from animal brain or from recombinant *E. coli* strains expressing animal IMPase. Although crude enzyme preparations can also be used it is preferable to use purified enzyme. The purified enzyme routinely has a specific activity of 25 $\mu$mol of Pi/min/mg of protein as determined in a standard assay (P. V. Attwood et al., Biochem. Jour., 1988, 253, pp. 387–394) with 4 mH 2-glycerolphosphate as substrate.

The enzyme activity may be determined according to A. J. Ganzhorn and M. C. Chanal, Biochem., 1990, 29; the reaction mixture contains 50mM Tris-HCl, pH 7.5, 2 mM magnesium chloride and 0.1 mM EGTA. Then, 5 ug/ml of IMPase and 4 mM of 2-glycerolphosphate substrate are added to the reaction mixture; alternatively, it is also possible to add the substrate directly into the reaction mixture, before adding the enzyme.

The reaction is considered terminated after 30 minutes from the addition of the substrate or the enzyme (depending on which one is added later); the liberated phosphate is determined by molybdate coloration (P. V. Attwood et al., Biochem. Jour., 1988, 253, pp. 387–394) at 350 nm with a Shimadzu spectrophotometer UV 2100.

The enzyme reaction is performed either in the absence or in the presence of various concentrations of 6'β-Stachybotrydial or MDL63394 to determine the amount of inhibitor required to inhibit the enzyme activity by 50% (IC50); the results are reported in Table 1, compared with the activity of L-671,776.

TABLE 1

| Compound | IC50 ugs/ml |
|---|---|
| 6'β-Stachybotrydial | 25 |
| MDL63394 | 80 |
| L-671,776 | 180 |

The same results are obtained when the above assay is performed at 37° C.

On the basis of the above results, the compounds 6'β-Stachybotrydial and MDL63394 may find application in the therapeutic field as anti-manic and anti-depressive agents.

Furthermore, the compounds of the invention can be used in an analythical method for detecting IMPase.

For the treatment of manic or depressive symphtoms, the compounds of the invention can be administered as such or formulated with pharmaceutically acceptable carriers; the administration may be done orally, parenterally or rectally.

For oral administration, the compounds of the invention can be formulated into solid or liquid preparations such as capsules, pills, tablets, troches, powder, syrups, solutions, suspensions or emulsions.

For preparing solid compositions such as tablets, the principal active ingredient is mixed with a pharmaceutical carrier, i.e. conventional tableting ingredients such as lactose, sucrose and cornstarch in combination with binders, such as acacia, cornstarch or gelatin, disintegrating agents such as potato starch or alginic acid, lubricants such as stearic acid or magnesium stearate and other pharmaceutical diluents, e.g. water, to form a solid preformulation composition containing a homogeneous mixture,. then referring to these preformulation compositions as homogeneous, it is meant that the active ingredient is dispersed evenly throughout the composition, so that the composition may be readily subdivided into equally effective unit dosage forms such as tablets, pills, capsules, and the like. This solid preformulation composition is then subdivided into unit dosage forms of the type described above containing from 50 to about 350 mg of the active ingredient of the present invention. The tablets or pills of the novel compositions can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in the release.

The liquid forms in which the novel composition of the present invention may be incorporated for oral administration include aqueous solutions, suitably flavored syrups, aqueous or oil suspensions, flavored emulsions with edible oils such as cottonseed oil, sesame oil, coconut oil, peanut oil and the like, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone, gelatin and the like.

For parenteral administration, the compounds of the invention may be formulated into suitable injectable preparations containing a liquid vehicle. Such vehicle normally has no therapeutic effect and should not be toxic. Examples of suitable vehicles for preparing injectable dosage forms of the compounds of the invention are water, aqueous vehicles (e.g. Sodium chloride injections, Dextrose injections, etc.), water miscible solvents (e.g. ethyl alcohol, polyethylene glycol, propylene glycol, etc.) and non-aqueous vehicles (e.g. "fixed oils" such as corn oil, cottonseed oil, peanut oil and sesame oil). Optionally, the injectable preparation may further contain buffers for stabilizing the solution (e.g. citrates, acetates and phosphates) and/or antioxidants (e.g. ascorbic acid or sodium bisulfite). The desired route of parenteral administration will place requirements on the specific formulation. For example, suspensions would not be administered directly in the blood stream because of the danger of insoluble particles blocking capillaries, whilst solutions to be administered subcutaneously would require strict attention to tonicity adjustment, otherwise irritation of the nerve endings in the anatomical area would give rise to pronounced pain.

Useful indications for the preparations of suitable oral, parenteral or rectal dosage forms can be found in: Remington's Pharmaceutical Sciences, 17th Edition, 1985, 1985 (Merck Publishing Company, Easton, Pennsylvania).

The dosage of the active ingredient depends on many factors which include type, age and conditions of the patient, specific active ingredient and formulation selected for the administration, administration schedule, etc. In general, a dosage level of about 10–20 mg/kg/day, on a regimen of 1–4 times a day, is preferred.

It is understood that the exact treatment level will depend upon the case history of the patient being treated and in the last analysis the precise treatment level falling within the above guidelines is left to the discretion of the therapist.

The present invention will be illustrated more in detail by the following examples.

EXAMPLE 1

Fermentation method for obtaining the IMPase-inhibiting complex

A 2 ml portion of frozen culture ATCC20928 in glycerol is defrozen and aseptically transferred to three slants containing solid medium PCA (mashed potato 20 g/l, mashed carrot 20 g/l, agar 20 g/l). Approximately 10 days later, a slant is used to inoculate a 500 ml baffled Erlenmeyer flask containing 100 ml of sterile medium (pH 6.8) containing tomato paste (40 g/l), atomized corn steep (5 g/l), starch potato (10 g/l), glucose (10 g/l) and 10 ml of trace elements mix. The trace element mix contains $FeSO_4.7H_2O$ (1 g/l), $MnSO_4.4H_2O$ (1 gl), $CuCl_2.2H_2O$ (25 mg/l), $CaCl_2.2H_2O$ (100 mg/l), $H_3BO_3$ (56 mg/l), $(NH_4)_6Mo_7O_{24}.4H_2O$ (19 mg/l) and $ZnSO_4.7H_2O$ (200 mg/l).

The mixture is incubated at 25° C. on 150 rpm, for 3 days.

Five percent inoculum is used to inoculate 15 liters fermenter containing 12 liters of seed medium, prepared as above described. The fermentation is carried out at 25° C. under a 6 liters/minutes range of airflow and agitation rate (200–500 rpm) for about 4 days.

EXAMPLE 2

Recovery of the IMPase-inhibiting complex from the fermentation mixture 81 of the mixture fermented according to Example 1 are harvested and the mycelium is removed by filtration with Hyflo filter matrix. The IMPase-inhibiting complex is adsorbed from the filtrate (3 hours stirring, batch-wise) onto 250 ml of S112 polystyrene resin (The Dow Chemical Company). The resin is then recovered, washed with water and eluted with 1 l of EtOH. The eluates are concentrated under reduced pressure and the aqueous residue lyophilized to yield crude IMPase-inhibiting complex.

EXAMPLE 3

Purification of the IMPase-inhibiting complex and isolation of individual factors L-671,776, 6'β-Stachybotrydial and MDL63394.

The crude preparation (obtained according to example 2) is suspended in acetone, the precipitate is separated by centrifuge and discarded. The surnatant is concentrated under reduced pressure and the obtained sample (3 g) is then applied to the top of a silica gel column (470×30 mm, particle size 230–400 mesh ASTM, Merck 9385) previously equilibrated with hexane.

A stepwise fractionation of the crude mixture is carried out with a medium pressure apparatus (BUCHI Preparative LC-system B680 A) by eluting at a flow rate of 35 ml/min with increasing amounts of acetone (Solvent B) in hexane (solvent A) according to the following gradient:

from 0% B to 40% B in 120 minutes,
isocratic at 40% B for 10 minutes and
from 40% B to 100% B in 20 minutes.

Fractions of 35 ml are collected and each fraction is analyzed by TLC (on silica gel using hexane:acetone, 6:4, as mobile phase) and tested for IMPase-inhibiting activity (according to the above cited A. J. Ganzhorn and M. C. Chanal, Biochem., 1990, 29).

Those fractions containing the same single factor are pooled, brought to dryness, redissolved in t-butanol and lyophilized, obtaining the pure compounds L-671,776, 6'β-Stachybotrydial and HDL63394.

TLC analysis of the three factors on silica gel using hexane:acetone (6:4) as mobile phase, shows the following $R_f$ values:

compound L-671,776=0.26;
6'β-Stachybotrydial=0.48;
MDL63394=0.23.

We claim:

1. A Sesquiterpenic compound having the following physico-chemical characteristics:

A) Ultraviolet absorption spectrum:

| Solvent | Lambda max (nm) |
| --- | --- |
| MeOH | 222, 284 |
| 0.1 M KOH | 231, 291, 334 |

B) Positive ion FAB spectrum on a Finnigan TSQ 700 triple stage quadrupole mass spectrometer; saddle field atom gun with Xe gas at 8 kV voltage and 0.23 mA current; glycerol/water matrix:

Major FAB/MS peak determined at 387 (MH+)

C) $R_f$ value of 0.48 in the following TLC system: hexane:acetone, 6:4 (v/v) on silica gel D) NMR spectra recorded in $CDCl_3$ with a Bruker AM 500 instrument, using TMS as internal standard (δ,ppm=0), (s=singlet; d=doublet; br s=broad singlet; m=multiplet):

1H-NHR recorded at 500 MHz, (δ,ppm): 10.65 s, 10.40 s, 6.94 s, 3.41 br s, 3.19 d, 2.84 d, 2.00–1.72 m, 1.70–1.40 m, 1.02 2 m, 0.89 s, 0.77 s;

$^{13}$C-NMR recorded at 125.76 MHz, (δ,ppm): 193.5, 188.6, 167.6, 157.5, 138.1, 119.5, 111.5, 109.1, 100.7, 75.7, 42.3, 40.1, 37.6, 37.1, 31.2, 30.7, 28.3, 24.7, 24.2, 22.3, 21.0, 16.1, 15.5.

2. A Sesquiterpenic compound having the following physico-chemical characteristics:

A) Ultraviolet absorption spectrum:

| Solvent | Lambda max (nm) |
| --- | --- |
| MeOH | <200, 275 |
| 0.1 M KOH | <200, 282, 337 |

B) Positive ion FAB spectrum on a Finnigan TSQ 700 triple stage quadrupole mass spectrometer; saddle field atom gun with Xe gas at 8 kV voltage and 0.23 mA current; glycerol/water matrix:

Major FAB/MS peak determined at 403 (MH+)
C) $R_f$ value of 0.23 in the following TLC system: hexane:acetone, 6:4 (v/v) on silica gel.

3. A Compound of formula IV

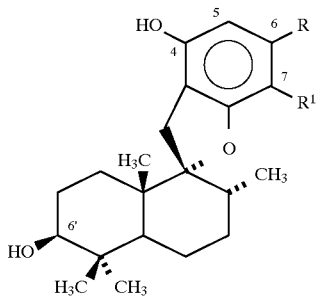

wherein R and $R^1$ represent both a —CHO moiety or one of R or $R^1$ represents a —CHO moiety and the other represents a —COOH moiety.

4. A Process for preparing a compound according to claims 1, 2 or 3 which comprises:
   a) cultivating Under aerobic conditions in an aqueous nutrient medium containing assimilable sources of carbon, nitrogen, and inorganic salts a fungus of the Memnoniella genus capable of producing a IMPase-inhibiting complex containing the IMPase-inhibiting compounds 6'β-Stachybotrydial and/or MDL63394;
   b) recovering the IMPase-inhibiting complex from the fermentation broth and/or from the mycelium;
   c) purifying the obtained crude complex and isolating the compounds 6'β-Stachybotrydial and/or MDL63394.

5. A Process according to claim 4 wherein the fungus of the genus Memnoniella is *Memnoniella echinata* ATCC 20928 or a IMPase-inhibiting complex producing variant or mutant thereof.

6. A process according to claim 4 wherein the IMPase-inhibiting complex is recovered from the mycelium by extracting the filtered or centrifuged mycelium with a water-miscible organic solvent, concentrating the extracts and recovering the crude IMPase-inhibiting complex by precipitation, by extraction of the concentrated aqueous residue with a water-immiscible organic solvent or by adsorption chromatography followed by elution of the desired product from the adsorption matrix.

7. A process according to claim 4 wherein the single factors of the IMPase-inhibiting complex are separated by means of chromatographic techniques.

8. A process according to claim 7 wherein the single factors of the IMPase-inhibiting complex are separated by means of HPLC, using silica gel as stationary phase and hexane/acetone as mobile phase.

9. A Compound according to claim 1, 2 or 3 for use as medicament.

10. A Pharmaceutical composition containing a compound of any one of claims 1, 2 or 3 as the active ingredient in admixture with a pharmaceutically acceptable carrier.

11. A Pharmaceutical composition according to claim 10 for the treatment of mania and depression symphtoms.

12. A Method for treating maniac and depressive symphtoms which comprises administering an effective amount of a compound of any one of claim 1, 2 or 3 to a patient in need thereof.

* * * * *